US012765867B2

(12) United States Patent
Fujii

(10) Patent No.: US 12,765,867 B2
(45) Date of Patent: Oct. 20, 2026

(54) ULTRASOUND TOMOGRAPHIC IMAGE DISPLAY CONTROL DEVICE AND ULTRASOUND TOMOGRAPHIC IMAGE DISPLAY CONTROL PROGRAM

(71) Applicant: FUJIFILM Corporation, Tokyo (JP)

(72) Inventor: Nobuhiko Fujii, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 19/268,997

(22) Filed: Jul. 14, 2025

(65) Prior Publication Data

US 2026/0020844 A1 Jan. 22, 2026

(30) Foreign Application Priority Data

Jul. 16, 2024 (JP) ................................ 2024-113643

(51) Int. Cl.
*A61B 8/00* (2006.01)
*G06T 3/60* (2006.01)

(52) U.S. Cl.
CPC .............. *A61B 8/54* (2013.01); *A61B 8/4263* (2013.01); *A61B 8/463* (2013.01); *G06T 3/60* (2013.01)

(58) Field of Classification Search
CPC ......... A61B 8/54; A61B 8/4263; A61B 8/463; G06T 3/60
See application file for complete search history.

(56) References Cited

U.S. PATENT DOCUMENTS

2015/0342563 A1 12/2015 Takahashi
2024/0197403 A1* 6/2024 Mino ..................... A61B 10/04

FOREIGN PATENT DOCUMENTS

JP 2013-255658 A 12/2013
JP 2015-226607 A 12/2015
JP 2017029209 A * 2/2017 ........... A61B 8/4455

* cited by examiner

*Primary Examiner* — Gerald Johnson

(74) *Attorney, Agent, or Firm* — Studebaker Brackett PLLC

(57) ABSTRACT

An image forming unit forms an ultrasound tomographic image representing a cross section of a target tissue, based on a received signal obtained by transmission and reception of ultrasound waves to and from the target tissue of a subject by an ultrasound probe. A probe detection unit detects a posture of the ultrasound probe. In a case where the posture of the ultrasound probe is a reversed posture in which one end side of the ultrasound probe faces a direction opposite to a prescribed direction predetermined for the target tissue, a display controller flips the ultrasound tomographic image horizontally and displays the ultrasound tomographic image on a display.

7 Claims, 11 Drawing Sheets

ULTRASOUND TOMOGRAPHIC IMAGE DISPLAY CONTROL DEVICE AND ULTRASOUND TOMOGRAPHIC IMAGE DISPLAY CONTROL PROGRAM

CROSS REFERENCE TO RELATED APPLICATION

This application claims priority to Japanese Patent Application No. 2024-113643 filed on Jul. 16, 2024, which is incorporated herein by reference in their entireties including the specifications, claims, drawings, and abstracts.

BACKGROUND OF THE INVENTION

1. Field of the Invention

The present specification discloses improvements in an ultrasound tomographic image display control device and an ultrasound tomographic image display control program.

2. Description of the Related Art

An ultrasound diagnostic device is known that transmits ultrasound waves from an ultrasound probe to a subject, receives reflected waves from the subject using the ultrasound probe, and performs various types of processes, such as formation of an ultrasound tomographic image representing a cross section in the subject, formation of a Doppler image representing a velocity of a tissue (blood or the like) in the subject, and various types of measurement, based on a received signal formed from the reflected waves.

In the related art, various techniques that detect a posture of an ultrasound probe to support an examiner have been proposed.

For example, JP2013-255658A discloses an ultrasound diagnostic device including: an ROI mark setting unit that sets a region of interest designated by an examiner on an ultrasound image; a camera that images a subject, to which a subject AR mark has been attached, and an ultrasound probe, to which an ultrasound probe AR mark has been attached, to acquire a captured image; a non-subject coordinate conversion unit that calculates a body surface curve approximating a body surface of the subject based on the subject AR mark in the captured image; an ultrasound probe coordinate conversion unit that calculates 3D coordinate information of the ultrasound probe based on the ultrasound probe AR mark in the captured image; a 3D processor that calculates a position of the region of interest on the body surface of the subject based on the region of interest, the body surface curve of the subject, and the 3D coordinate information of the ultrasound probe; and an ROI/captured image combination unit that displays an ROI projection mark indicating the position of the region of interest to be superimposed on the captured image.

In addition, JP2015-226607A discloses an ultrasound diagnostic device that images a subject and an ultrasound probe with a camera to form a visual field image, performs a contour extraction process on the visual field image to specify a distal end position of the ultrasound probe, and displays a mark indicating the specified distal end position of the ultrasound probe on a body mark representing the subject.

SUMMARY OF THE INVENTION

However, in a case where the ultrasound tomographic image formed by the ultrasound diagnostic device is displayed on a display unit, display orientation (in other words, a display rule) of the ultrasound tomographic image in a left-right direction may be predetermined. The display orientation of the ultrasound tomographic image in the left-right direction means which side (for example, a foot side) in a real space a right side of the ultrasound tomographic image corresponds to and which side (for example, a head side) in the real space a left side of the ultrasound tomographic image corresponds to. Further, in the present specification, the right side (left side) means a right side (left side) in a case where the ultrasound tomographic image is viewed such that a side on which a depth of field is shallow (body surface side) is an upper side and a side on which the depth of field is deep is a lower side.

The display rule is often determined for each target tissue (for example, an organ) to be depicted in the ultrasound tomographic image. For example, in the ultrasound tomographic image in which a liver is depicted, a display rule saying "the ultrasound tomographic image is displayed such that a right side of the ultrasound tomographic image is a foot side in a real space and a left side of the ultrasound tomographic image is a head side in the real space" is determined.

FIG. 17A is a diagram showing a state in which an ultrasound probe P is brought into contact with a subject E. Here, it is assumed that an operator, such as a doctor, is trying to form an ultrasound tomographic image of the liver of the subject E. In a case where the ultrasound probe P is a 1D ultrasound probe having a plurality of transducers arranged in one direction (array direction), scanning is performed in the array direction with an ultrasound beam transmitted from the ultrasound probe P. Then, an ultrasound tomographic image representing a scanning plane of the ultrasound beam is formed. Since the ultrasound tomographic image represents the scanning plane of the ultrasound beam, which orientation in the real space the right side or the left side of the ultrasound tomographic image corresponds to is determined according to the posture of the ultrasound probe P.

In this example, the side of one end Pa of the ultrasound probe P corresponds to the right side of the ultrasound tomographic image. Therefore, the operator brings the ultrasound probe P into contact with the subject E such that the ultrasound probe P is in a posture in which the side of the one end Pa faces the foot side. Therefore, as shown in FIG. 17B, an ultrasound tomographic image in which the right side is the foot side and the left side is the head side is formed and displayed.

However, as shown in FIG. 18A, in some cases, the ultrasound probe P needs to be brought into contact with the subject E in a posture in which the side of the one end Pa of the ultrasound probe P faces the head side for some reason (for example, in a case where it is desired to form an ultrasound tomographic image of an edge of the liver in laparotomy, but the ultrasound probe P or a cord comes into contact with an abdominal wall). In this case, as shown in FIG. 18B, an ultrasound tomographic image in which the right side is the head side and the left side is the foot side is formed and displayed. That is, the ultrasound tomographic image does not conform to the predetermined display rule.

In the related art, the ultrasound diagnostic device has a flip display function of flipping the ultrasound tomographic image horizontally and displaying the ultrasound tomographic image. Therefore, as shown in FIG. 18B, in a case where the left-right direction of the ultrasound tomographic image is opposite to the display rule, the flip display function may be used to flip the ultrasound tomographic image horizontally. However, the operator needs to input an instruction for the ultrasound tomographic image in order to flip the ultrasound tomographic image horizontally, which requires time and effort. In particular, for example, in a case where an operating surgeon is in a sterile field and an ultrasound diagnostic device is disposed outside the sterile field, the operating surgeon needs to instruct the operator (for example, a nurse) outside the sterile field to flip the ultrasound tomographic image horizontally. As a result, the problem is more pronounced.

An object of an ultrasound tomographic image display control device disclosed in the present specification is to make display orientation of an ultrasound tomographic image displayed on a display unit in a left-right direction conform to a display rule, without requiring time and effort of an operator.

According to an aspect of the present invention, there is provided an ultrasound tomographic image display control device including: a probe detection unit that detects a posture of an ultrasound probe which performs scanning with an ultrasound beam to transmit and receive an ultrasound wave to and from a target tissue of a subject; and a display controller that displays, on a display unit, an ultrasound tomographic image formed based on a received signal based on a reflected wave from the target tissue. The display controller flips the ultrasound tomographic image horizontally and displays the ultrasound tomographic image in a case where the posture of the ultrasound probe is a reversed posture in which one end side of a scanning direction of the ultrasound beam faces a direction opposite to a prescribed direction predetermined for the target tissue.

The display controller may display, on the display unit, an image orientation indicator indicating one end side of the ultrasound tomographic image in the scanning direction.

The display controller may display the ultrasound tomographic image on the display unit, without flipping the ultrasound tomographic image horizontally, even in a case where the ultrasound probe is in the reversed posture while the ultrasound probe is transmitting and receiving the ultrasound wave to and from the target tissue. After the transmission and reception of the ultrasound wave to and from the target tissue are ended, the display controller may flip the ultrasound tomographic image, which has been formed based on the received signal acquired while the ultrasound probe is in the reversed posture, horizontally and may display the ultrasound tomographic image on the display unit.

The probe detection unit may further detect a position of the ultrasound probe, and the display controller may display a subject symbol that schematically represents an outward shape of the subject on the display unit, together with the ultrasound tomographic image, and may further display a probe symbol that represents the position and posture of the ultrasound probe to be superimposed on the subject symbol, based on the position and posture of the ultrasound probe detected by the probe detection unit.

The ultrasound tomographic image display control device may further include a camera that images the subject and the ultrasound probe. The display controller may display an image captured by the camera as the subject symbol and the probe symbol on the display unit.

The ultrasound tomographic image display control device may further include a notification processing unit that, in a case where the probe detection unit is not capable of detecting a position or the posture of the ultrasound probe, notifies a user that the position or posture of the ultrasound probe is not capable of being detected.

In addition, according to another aspect of the present invention, there is provided an ultrasound tomographic image display control program causing a computer to function as: a probe detection unit that detects a posture of an ultrasound probe which performs scanning with an ultrasound beam to transmit and receive an ultrasound wave to and from a target tissue of a subject; and a display controller that displays, on a display unit, an ultrasound tomographic image formed based on a received signal based on a reflected wave from the target tissue. The display controller flips the ultrasound tomographic image horizontally and displays the ultrasound tomographic image in a case where the posture of the ultrasound probe is a reversed posture in which one end side of a scanning direction of the ultrasound beam faces a direction opposite to a prescribed direction predetermined for the target tissue.

According to the ultrasound tomographic image display control device disclosed in the present specification, it is possible to make the display orientation of the ultrasound tomographic image displayed on the display unit in the left-right direction conform to the display rule, without requiring the time and effort of the operator.

DESCRIPTION OF THE PREFERRED EMBODIMENTS

Figure 1:
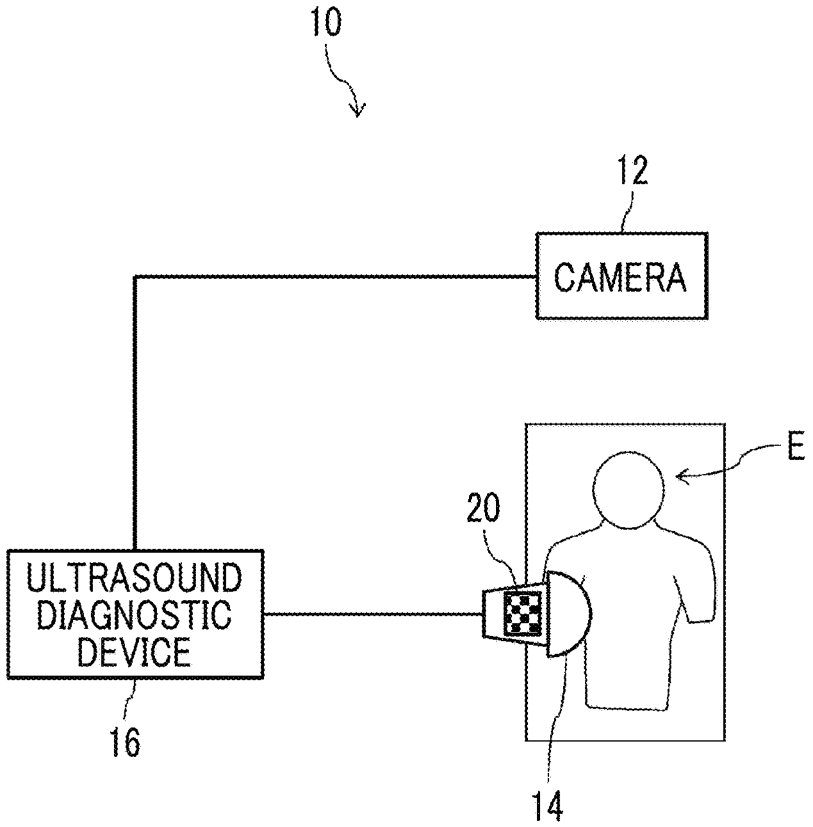
FIG. 1 is a schematic diagram showing a configuration of an ultrasound diagnostic system according to an embodiment.

FIG. 1 is a schematic diagram showing a configuration of an ultrasound diagnostic system 10 according to an embodiment. The ultrasound diagnostic system 10 is configured to include a camera 12 and an ultrasound diagnostic device 16 as an ultrasound tomographic image display control device including an ultrasound probe 14. The camera 12 and the ultrasound diagnostic device 16 are connected such that they can communicate with each other.

A probe detection marker 20 is attached to the ultrasound probe 14. The probe detection marker 20 is a mark that has a pattern indicating the position and posture of the ultrasound probe 14. An example of the probe detection marker 20 is an augmented reality (AR) marker.

The camera 12 is configured to include a processor configured as a CPU or the like and a communication interface configured as a network adapter or the like in addition to a lens and an image sensor. The camera 12 images a subject E and the ultrasound probe 14 (specifically, the probe detection marker 20). The camera 12 may be an extracorporeal camera that images a body surface of the subject E or may be an intracorporeal camera, such as an endoscope, inserted into the subject. A captured image is formed by the image sensor of the camera 12. The captured image is transmitted to the ultrasound diagnostic device 16 by the communication interface of the camera 12.

Figure 2:
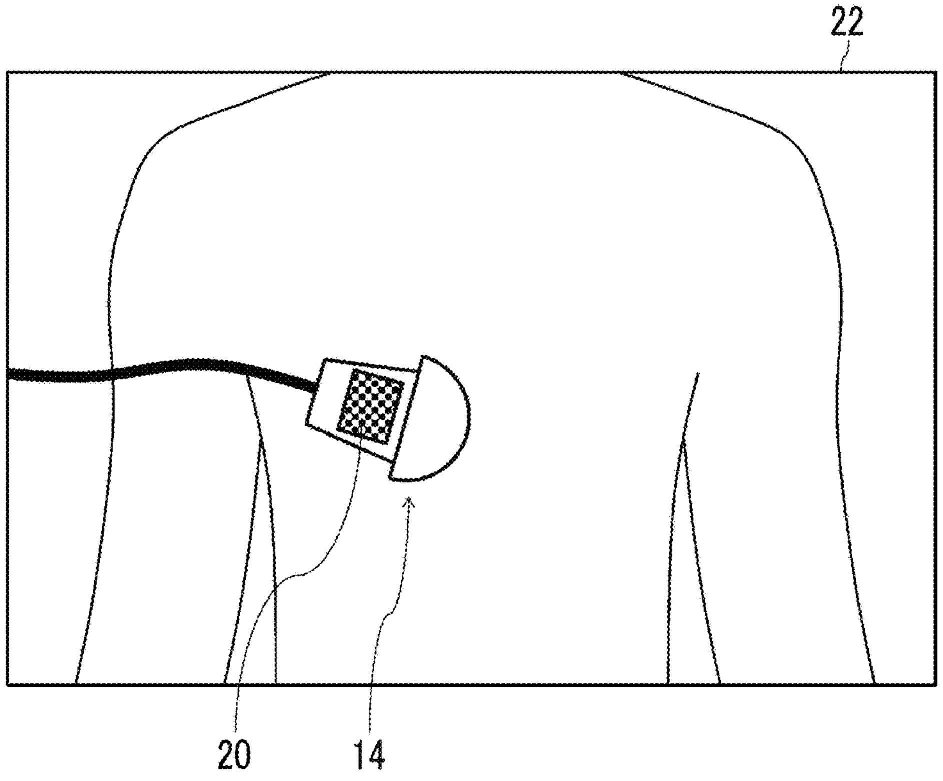
FIG. 2 is a diagram showing an example of an image captured by a camera.

FIG. 2 is a diagram showing an example of an image 22 captured by the camera 12. As described above, the captured image 22 includes an image of the probe detection marker 20. The ultrasound diagnostic device 16 can analyze the image of the probe detection marker 20 included in the captured image 22 to detect the position and posture of the ultrasound probe 14. A process of detecting the position and posture of the ultrasound probe 14 will be described in detail below.

Figure 3:
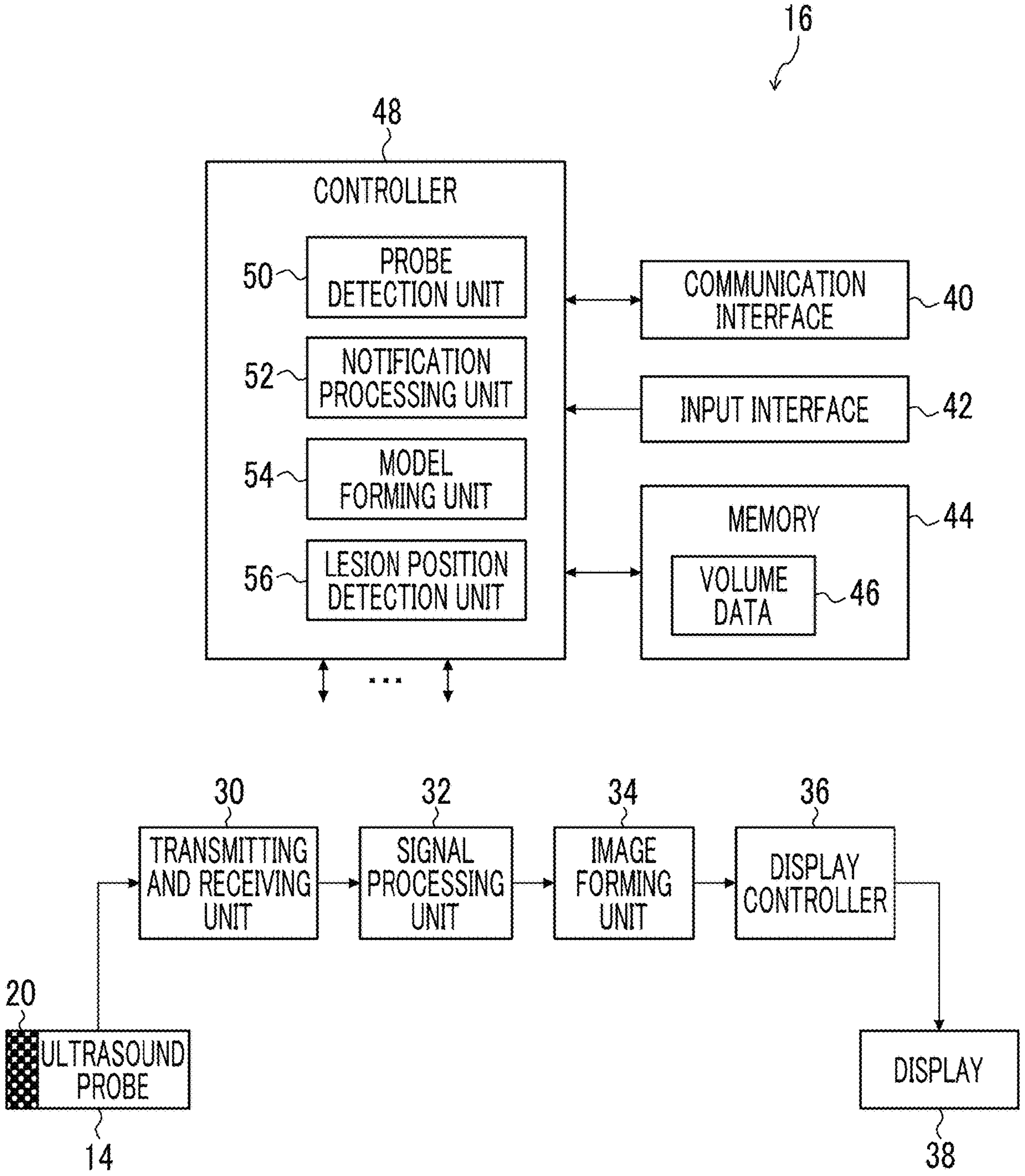
FIG. 3 is a schematic diagram showing a configuration of an ultrasound diagnostic device according to the present embodiment.

FIG. 3 is a schematic diagram showing a configuration of the ultrasound diagnostic device 16. The ultrasound diagnostic device 16 is a medical device that is installed in a medical institution such as a hospital.

The ultrasound probe 14 is a device that transmits and receives ultrasound waves to and from the subject E, particularly, a target tissue of the subject E. The ultrasound probe 14 has a transducer array consisting of a plurality of transducers that transmit and receive the ultrasound waves to and from the target tissue. In the ultrasound probe 14, the transducer array includes a plurality of transducers that are arranged in one direction (array direction). A transmission signal is supplied from a transmitting and receiving unit 30, which will be described below, to each transducer such that each transducer generates ultrasound waves. Specifically, the ultrasound probe 14 performs scanning with ultrasound beams in a plane (scanning plane) parallel to the array direction.

The probe detection marker 20 is attached to the ultrasound probe 14 as described above.

The transmitting and receiving unit 30 transmits the transmission signal to the ultrasound probe 14 (specifically, each transducer of the transducer array) under the control of a controller 48 which will be described below. In addition, the transmitting and receiving unit 30 receives a received signal from each transducer that has received reflected waves from the target tissue. The transmitting and receiving unit 30 includes an adder and a plurality of delayers corresponding to each transducer and performs a phasing addition process of matching and adding the phases of the received signals from each of the transducers using the adder and the plurality of delayers. Therefore, a received beam signal in which information indicating the signal intensity of the reflected waves from the target tissue is arranged in a depth direction of the target tissue is formed.

A signal processing unit 32 executes various types of signal processing including a filtering process of applying a bandpass filter and a detection process on the received beam signal from the transmitting and receiving unit 30.

An image forming unit 34 forms an ultrasound tomographic image (B-mode image) representing a cross section of the target tissue (particularly, the scanning plane of the ultrasound beams) based on the received beam signal subjected to the signal processing by the signal processing unit 32.

A display controller 36 performs control to display various images including the ultrasound tomographic image formed by the image forming unit 34 on a display 38.

The display 38 as a display unit is, for example, a display device configured as a liquid-crystal display, an organic electro-luminescence (EL) display, or the like.

The transmitting and receiving unit 30, the signal processing unit 32, the image forming unit 34, and the display controller 36 included in the ultrasound diagnostic device 16 are configured by a processor. The processor is configured to include at least one of a general-purpose processing device (for example, a CPU or the like) or a dedicated processing device (for example, a graphics processing unit (GPU), an application-specific integrated circuit (ASIC), a field-programmable gate array (FPGA), or a programmable logic device). The processor may be configured by cooperation between a plurality of processing devices that are present at physically separated positions, instead of being configured by one processing device. In addition, each of the above-described units may be implemented by cooperation between hardware, such as a processor, and software.

A communication interface 40 is configured as, for example, a network adapter. The communication interface 40 exhibits a function of communicating with another device (particularly, the camera 12). In particular, the communication interface 40 receives the captured image from the camera 12.

An input interface 42 is configured as, for example, buttons, a track ball, or a touch panel. The input interface 42 is used to input an instruction from an operator, who uses the ultrasound diagnostic device 16, to the ultrasound diagnostic device 16.

A memory 44 is configured to include a hard disk drive (HDD), a solid-state drive (SSD), an embedded MultiMediaCard (eMMC), a read-only memory (ROM), a random-access memory (RAM), or the like. An ultrasound tomographic image display control program for operating each unit of the ultrasound diagnostic device 16 is stored in the memory 44. In addition, the ultrasound tomographic image display control program can also be stored, for example, in a non-transitory computer-readable storage medium such as a Universal Serial Bus (USB) memory or a CD-ROM. The ultrasound diagnostic device 16 can read the ultrasound tomographic image display control program from the storage medium and execute the ultrasound tomographic image display control program. The ultrasound diagnostic device 16 reads the ultrasound tomographic image display control program to exhibit the functions which will be described below. Therefore, it can be said that the ultrasound diagnostic device 16 is a computer program product.

As shown in FIG. 3, volume data 46 is stored in the memory 44. The volume data 46 is formed by a model forming unit 54, which will be described below, and is stored in the memory 44. The volume data 46 will be described in detail below.

The controller 48 is configured to include at least one of a general-purpose processor (for example, a CPU or the like) or a dedicated processor (for example, a GPU, an ASIC, an FPGA, or a programmable logic device). The controller 48 may be configured by cooperation between a plurality of processing devices that are present at physically separated positions, instead of being configured by one processing device. The controller 48 controls each unit of the ultrasound diagnostic device 16. In addition, as shown in FIG. 3, the controller 48 functions as a probe detection unit 50, a notification processing unit 52, the model forming unit 54, and a lesion position detection unit 56 according to the ultrasound tomographic image display control program stored in the memory 44.

The probe detection unit 50 detects at least one of the position or posture of the ultrasound probe 14. In the present embodiment, the probe detection unit 50 analyzes the captured image 22 acquired by the camera 12 to detect the position and posture of the ultrasound probe 14. As described above, the captured image 22 includes the image of the probe detection marker 20 indicating the position and posture of the ultrasound probe 14 (see FIG. 2). The probe detection unit 50 analyzes the image of the probe detection marker 20 in the captured image 22 to detect parameters indicating the position and posture of the ultrasound probe 14. The parameter indicating the position of the ultrasound probe 14 may be, for example, three-dimensional coordinates in a camera coordinate system. The parameter indicating the posture of the ultrasound probe 14 may be a rotation angle about a prescribed axis in the camera coordinate system. In addition, since a known method can be used as a method of detecting the position and posture of the ultrasound probe 14 in the camera coordinate system from the image of the probe detection marker 20 included in the captured image 22, a detailed description thereof will be omitted here.

The probe detection unit 50 executes calibration before detecting the position and posture of the ultrasound probe 14 based on the captured image 22. Specifically, the operator sets the position and posture of the ultrasound probe 14 to a predetermined position and posture and inputs a calibration instruction to the ultrasound diagnostic device 16 in that state. The probe detection unit 50 detects the position and posture of the ultrasound probe 14 in a case where the calibration instruction is input, based on the probe detection marker 20 included in the captured image 22, and stores the detected position and posture as a reference position and a reference posture in the memory 44, respectively. Then, the probe detection unit 50 detects the position of the ultrasound probe 14 as a relative position with respect to a known reference position and detects the posture of the ultrasound probe 14 as a relative posture with respect to a known reference posture.

The probe detection unit 50 may detect at least one of the position or posture of the ultrasound probe 14 using a method other than the method of analyzing the captured image 22. For example, a position and posture sensor, such as a magnetic sensor or an acceleration sensor, may be provided in the ultrasound probe 14, and at least one of the position or posture of the ultrasound probe 14 in a real space may be detected based on a detection value of the position and posture sensor.

As described above, a left-right direction of the ultrasound tomographic image is determined according to the posture of the ultrasound probe 14. Therefore, the display controller 36 displays the ultrasound tomographic image formed by the image forming unit 34 on the display 38 according to the posture of the ultrasound probe 14 detected by the probe detection unit 50 such that the ultrasound tomographic image conforms to a predetermined display rule.

Figure 4:
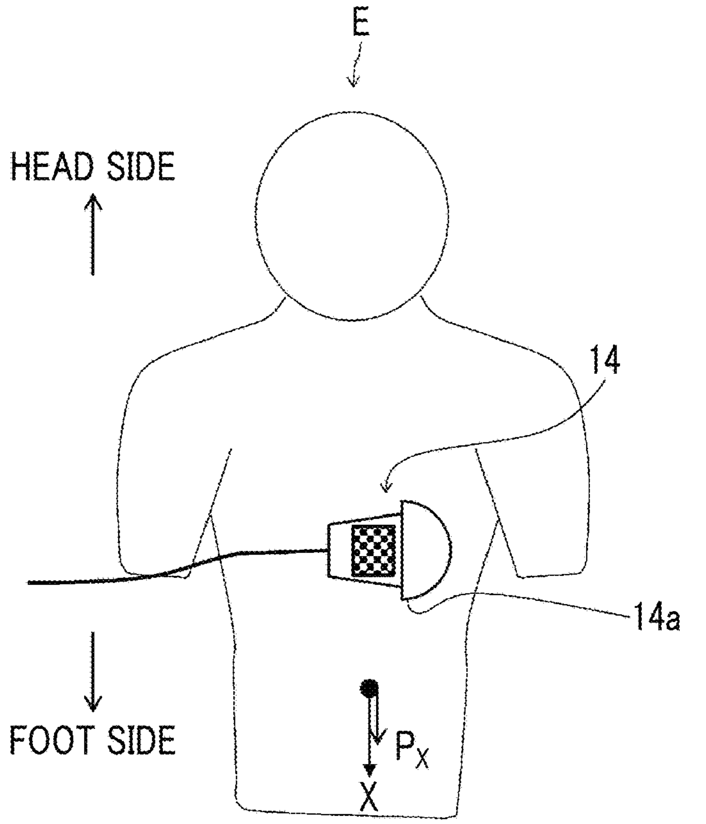
FIG. 4 is a diagram showing a first state in which an ultrasound probe is brought into contact with a subject in the present embodiment.

A process of displaying the ultrasound tomographic image (particularly, a process of flipping the ultrasound tomographic image horizontally) will be described in detail with reference to FIGS. 4 to 7. FIG. 4 is a diagram showing a first state in which the ultrasound probe 14 is brought into contact with the subject E in the present embodiment. In this example, it is assumed that an operator, such as a doctor, is trying to form an ultrasound tomographic image of a liver of the subject E. It is assumed that the calibration is performed in the posture of the ultrasound probe 14 shown in FIG. 4, that is, in the posture in which one end 14*a* of the ultrasound probe 14 faces a foot side. It is assumed that a direction in which the one end 14*a* of the ultrasound probe 14 faces during the calibration is an X-axis and the direction in which the one end 14*a* of the ultrasound probe 14 faces at the current time is represented by an arrow $P_X$. In the state shown in FIG. 4, the X-axis faces the foot side, and the arrow $P_X$ faces the X-axis (that is, the foot side) direction.

Further, in the present embodiment, the ultrasound probe 14 has the transducer array that is arranged in one direction (array direction) from the one end 14*a* to the other end of the ultrasound probe 14, and a scanning direction of the ultrasound beam is parallel to the array direction. Therefore, it can be said that the side of the one end 14*a* of the ultrasound probe 14 is one end side (for example, a scanning start end side) in the scanning direction of the ultrasound beam.

Figure 5:
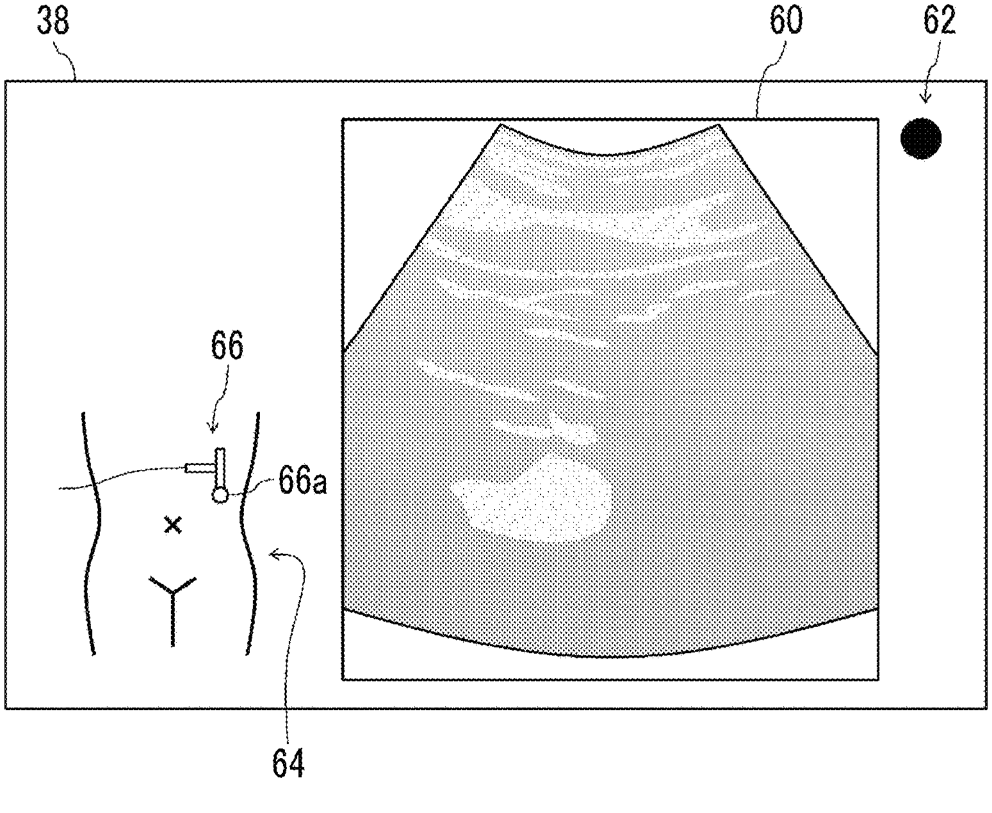
FIG. 5 is a first diagram showing a display example of an ultrasound tomographic image, a body mark, and a probe mark.

FIG. 5 is a diagram showing a display example of an ultrasound tomographic image 60 formed in a case where the position and posture of the ultrasound probe 14 are as shown in FIG. 4. As shown in FIG. 4, in a case where the ultrasound probe 14 is in the posture in which the one end 14*a* (that is, one end side in the scanning direction of the ultrasound beam) faces the X-axis direction, that is, the foot side, the image forming unit 34 forms the ultrasound tomographic image 60 of which the right side is the foot side in the real space, and the display controller 36 displays the ultrasound tomographic image 60. In this case, the displayed ultrasound tomographic image 60 conforms to the display rule for the ultrasound tomographic image 60 indicating the liver, which states that "the ultrasound tomographic image is displayed such that the right side of the ultrasound tomographic image is the foot side in the real space and the left side of the ultrasound tomographic image is the head side in the real space". Therefore, the display controller 36 displays the formed ultrasound tomographic image 60 on the display 38 without any change. In addition, as described above, the display orientation of the ultrasound tomographic image 60 in the left-right direction is determined by the posture of the ultrasound probe 14. Therefore, conformity to the display rule of the ultrasound tomographic image 60 indicating the target tissue can also mean that the posture of the ultrasound probe 14, which transmits and receives the ultrasound waves to and from the target tissue, conforms to a predetermined posture (a posture corresponding to the display rule of the ultrasound tomographic image 60).

The display controller 36 may display, on the display 38, an image orientation indicator indicating the side of the one end 14*a* of the ultrasound probe 14 (that is, the one end side in the scanning direction of the ultrasound beam) in the ultrasound tomographic image 60. In the example shown in FIG. 5, the display controller 36 displays an orientation mark 62 as the image orientation indicator. In the example shown in FIG. 5, since the right side of the ultrasound tomographic image 60 is the side of the one end 14*a* of the ultrasound probe 14, the display controller 36 displays the orientation mark 62 on the upper right side of the ultrasound tomographic image 60.

In addition, the display controller 36 may display a subject symbol that schematically represents an outward shape of the subject E on the display 38 together with the ultrasound tomographic image 60. In the example shown in FIG. 5, the display controller 36 displays a body mark 64 as the subject symbol. The body mark 64 is prepared in advance and is stored in the memory 44. A plurality of body marks 64 corresponding to the sizes of the subjects E may be stored in the memory 44, and the display controller 36 may display the body mark 64 corresponding to an instruction from the operator.

Further, the display controller 36 may display a probe symbol representing the position and posture of the ultrasound probe 14 to be superimposed on the body mark 64, based on the position and posture of the ultrasound probe 14 detected by the probe detection unit 50. In a case where the operator performs the calibration in a state in which the ultrasound probe 14 is placed at a prescribed position of the subject E, the display controller 36 can specify the position and posture of the probe symbol on the body mark 64, based on the position and posture of the ultrasound probe 14 detected by the probe detection unit 50 and the scale of the body mark 64. In the example shown in FIG. 5, the display controller 36 displays a probe mark 66 as the probe symbol. Similarly to the body mark 64, the probe mark 66 is prepared in advance and stored in the memory 44. As shown in FIG. 5, the probe mark 66 may include a one-end-side mark 66*a* indicating the one end 14*a* of the ultrasound probe 14. A plurality of probe marks 66 corresponding to the types of the ultrasound probes 14 may be stored in the memory 44, and the display controller 36 may display the probe mark 66 corresponding to the type of the ultrasound probe 14 connected to a device main body of the ultrasound diagnostic device 16.

The display of the subject symbol and the probe symbol enables the operator to easily recognize which part of the subject E the displayed ultrasound tomographic image 60 represents in cross section.

Figure 6:
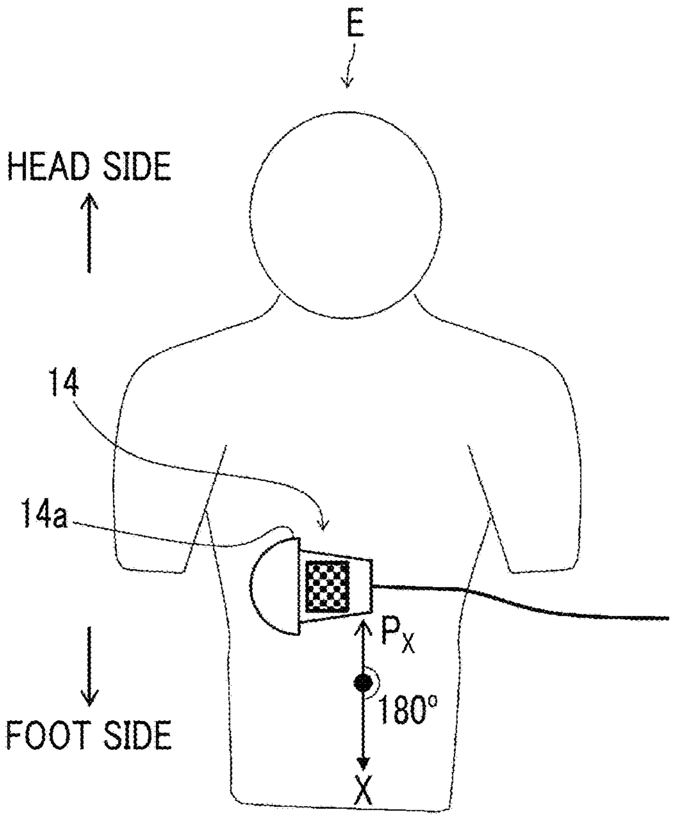
FIG. 6 is a diagram showing a second state in which the ultrasound probe is brought into contact with the subject in the present embodiment.

FIG. 6 is a diagram showing a second state in which the ultrasound probe 14 is brought into contact with the subject E in the present embodiment. In a case where the ultrasound waves are transmitted to and received from the liver of the subject E, the posture of the ultrasound probe 14 may need to be set to a posture in which the one end 14*a* faces the head side for some reason described above, as shown in FIG. 6. In addition, in a case where the calibration is performed in a posture in which the one end 14*a* of the ultrasound probe 14 faces the foot side (see FIG. 4) and the direction facing the foot side is the X-axis, the posture of the ultrasound probe 14 in which the one end 14*a* faces the head side can be expressed as a posture in which an angle formed between the X-axis and the arrow $P_X$ (direction in which the one end 14*a* of the ultrasound probe 14 faces) is 180° in a plan view.

Figure 7:
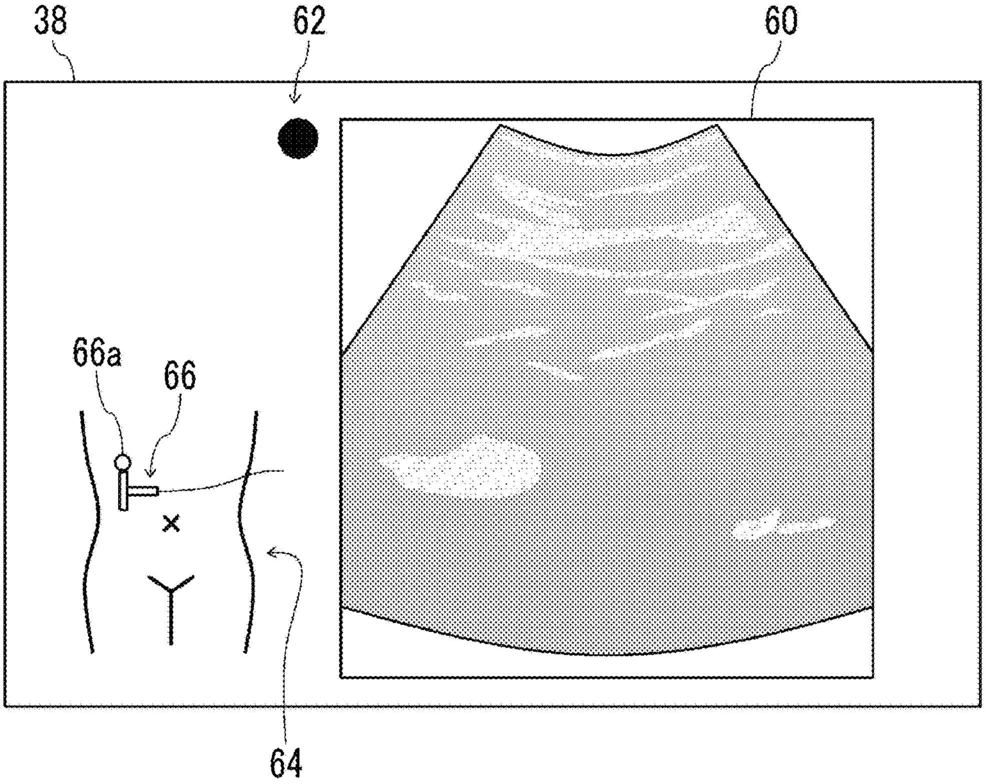
FIG. 7 is a second diagram showing a display example of the ultrasound tomographic image, the body mark, and the probe mark.

FIG. 7 is a diagram showing a display example of the ultrasound tomographic image 60 formed in a case where the ultrasound probe 14 is in the position and posture shown in FIG. 6. As shown in FIG. 6, in a case where the ultrasound probe 14 is in the posture in which the side of the one end 14*a* faces a direction opposite to the X-axis direction, that is, the head side, the image forming unit 34 forms the ultrasound tomographic image 60 of which the right side is the head side in the real space. Here, in a case where the display controller 36 displays the ultrasound tomographic image 60 on the display 38, the ultrasound tomographic image 60 of which the right side is the head side is displayed and does not conform to the display rule of the ultrasound tomographic image 60 indicating the liver. Therefore, in a case where the posture of the ultrasound probe 14 is a reversed posture in which the side of the one end 14*a* faces the direction opposite to the X-axis direction, that is, the head side, in other words, in a case where the posture of the ultrasound probe 14 is the reversed posture in which the side of the one end 14*a* faces a direction opposite to a prescribed direction (in this example, the foot side) predetermined for the target tissue, the display controller 36 flips the ultrasound tomographic image 60 horizontally and displays the ultrasound tomographic image 60.

As described above, the display controller 36 automatically flips the ultrasound tomographic image 60 horizontally and displays the ultrasound tomographic image 60 according to the posture of the ultrasound probe 14. Therefore, the display orientation of the ultrasound tomographic image 60 in the left-right direction can conform to the display rule, without requiring the time and effort of the operator.

Even in a case where the display controller 36 flips the ultrasound tomographic image 60 horizontally and displays the ultrasound tomographic image 60, the display controller 36 may display, on the display 38, the orientation mark 62 as the image orientation indicator indicating the side of the one end 14*a* of the ultrasound probe 14 in the ultrasound tomographic image 60. In this case, since the left side of the ultrasound tomographic image 60 is the side of the one end 14*a* of the ultrasound probe 14, the display controller 36 displays the orientation mark 62 on the upper left side of the ultrasound tomographic image 60. In other words, the operator can recognize that the ultrasound tomographic image 60 is flipped horizontally and displayed since the orientation mark 62 is displayed on the left side of the ultrasound tomographic image 60.

In the present embodiment, in a case where the calibration is performed in the posture in which the one end 14*a* of the ultrasound probe 14 faces the foot side (see FIG. 4), the direction facing the foot side is the X-axis, and the angle formed between the X-axis and the arrow $P_X$ (the direction in which the one end 14*a* of the ultrasound probe 14 faces) satisfies a prescribed condition in a plan view, the display controller 36 determines that the posture of the ultrasound probe 14 is the reversed posture, flips the ultrasound tomographic image 60 horizontally, and displays the ultrasound tomographic image 60. In the present embodiment, in a case where the angle formed between the X-axis and the arrow $P_X$ is equal to or greater than 180°, the display controller 36 determines that the posture of the ultrasound probe 14 is the reversed posture, flips the ultrasound tomographic image 60 horizontally, and displays the ultrasound tomographic image 60. Alternatively, in a case where the angle formed between the X-axis and the arrow $P_X$ is equal to or greater than 90° and less than 270°, the display controller 36 may determine that the posture of the ultrasound probe 14 is the reversed posture, flip the ultrasound tomographic image 60 horizontally, and display the ultrasound tomographic image 60.

The operator who checks the ultrasound tomographic image 60 displayed on the display 38 while bringing the ultrasound probe 14 into contact with the subject E recognizes the posture of the ultrasound probe 14 brought into contact with the subject E. Therefore, in a case where the ultrasound tomographic image 60 that has been flipped horizontally is displayed, the operator may be confused. In order to prepare for this case, the display controller 36 may display the ultrasound tomographic image 60 on the display 38, without flipping the ultrasound tomographic image 60 horizontally, even in a case where the ultrasound probe 14 is in the reversed posture while the ultrasound waves are being transmitted to and received from the target tissue (in a case where the ultrasound tomographic image 60 is displayed in real time). Then, after the transmission and reception of the ultrasound waves to and from the target tissue are ended, the display controller 36 may flip the ultrasound tomographic image 60, which has been formed based on the received signal acquired while the ultrasound probe 14 is in an inverted posture, horizontally and display the ultrasound tomographic image 60 on the display 38.

In this case, the probe detection unit 50 stores each received signal obtained by transmitting and receiving the ultrasound waves to and from the target tissue or each ultrasound tomographic image 60 formed from the received signal in the memory 44 in association with posture information indicating the posture of the ultrasound probe 14 in a case where the received signal has been obtained. Then, in a case where the ultrasound tomographic image 60 formed from the received signal is displayed afterward (the ultrasound tomographic image 60 is not displayed in real time) and the posture information associated with the ultrasound tomographic image 60 to be displayed or the received signal, which is the source of the ultrasound tomographic image 60, indicates that the posture of the ultrasound probe 14 is the reversed posture, the display controller 36 flips the ultrasound tomographic image 60 horizontally and displays the ultrasound tomographic image 60.

Figure 8:
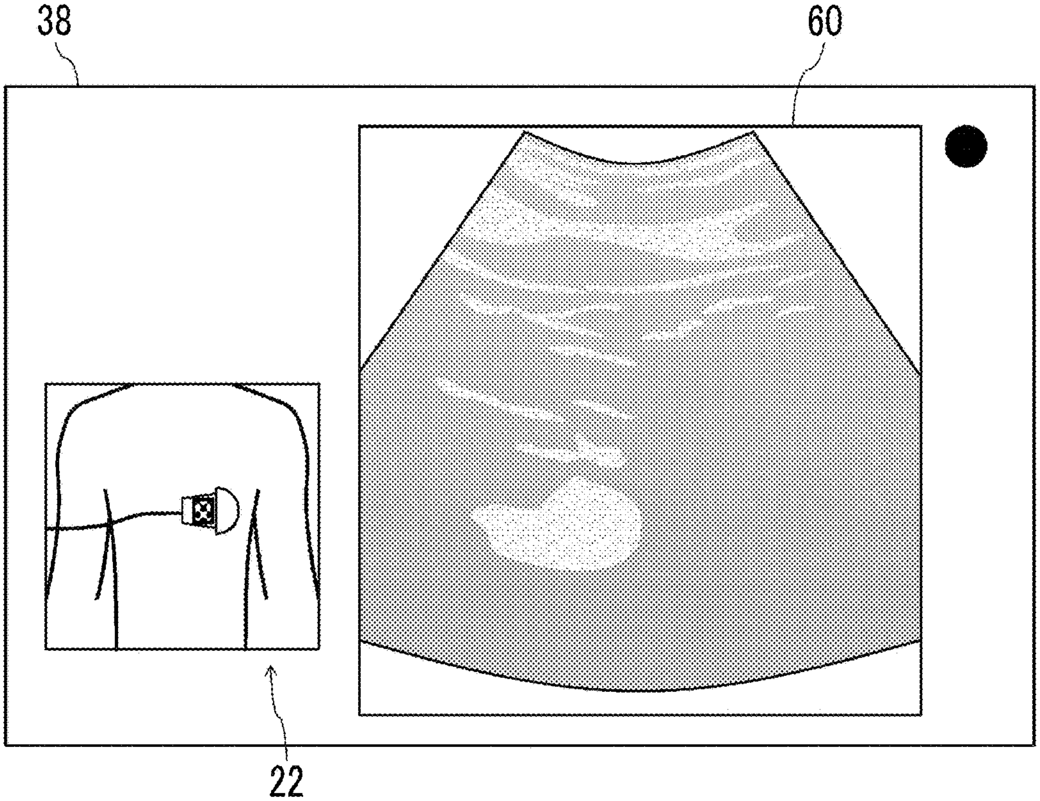
FIG. 8 is a diagram showing a display example of the ultrasound tomographic image and a captured image.

FIG. 8 is a diagram showing a display example of the ultrasound tomographic image 60 and the captured image 22. The display controller 36 may display the captured image 22 formed by imaging the subject E and the ultrasound probe 14 with the camera 12 as the subject symbol and the probe symbol on the display 38, instead of the body mark 64 and the probe mark 66. Since the captured image 22 shows the subject E and the ultrasound probe 14, the operator can more accurately recognize which part of the subject E the displayed ultrasound tomographic image 60 represents in cross section from the captured image 22 than from the body mark 64 and the probe mark 66.

Figure 9:
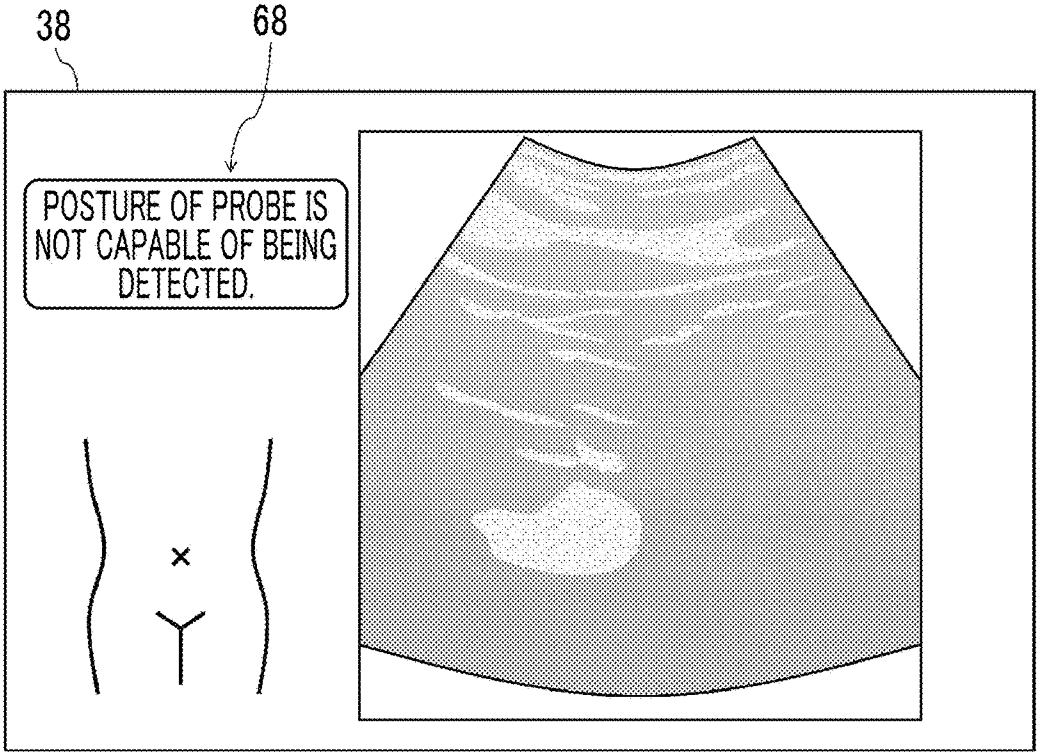
FIG. 9 is a diagram showing an example of notification that a posture of the ultrasound probe is not capable of being detected.

In a case where the probe detection unit 50 is not capable of detecting the position or posture of the ultrasound probe 14, the notification processing unit 52 notifies the user that the position or posture of the ultrasound probe 14 is not capable of being detected. For example, in a case where the image of the probe detection marker 20 is not included in the captured image 22 because an obstacle is interposed between the camera 12 and the probe detection marker 20, the probe detection unit 50 is not capable of detecting the position and posture of the ultrasound probe 14. In this case, there is no guarantee that the displayed ultrasound tomographic image 60 conforms to the display rule. Therefore, in this case, the notification processing unit 52 notifies the user that the position or posture of the ultrasound probe 14 is not capable of being detected. For example, as shown in FIG. 9, the notification processing unit 52 displays a message 68 saying "The posture of the probe is not capable of being detected" on the display 38. Of course, the notification indicating that the position or posture of the ultrasound probe 14 is not capable of being detected is not limited to the message 68. For example, the notification processing unit 52 may display some indicator on the display 38 or may output voice to perform the notification.

The model forming unit 54 forms a target tissue model representing the shape of the target tissue of the subject E. A process of forming the target tissue model via the model forming unit 54 will be described with reference to FIGS. 10 and 11.

Figure 10:
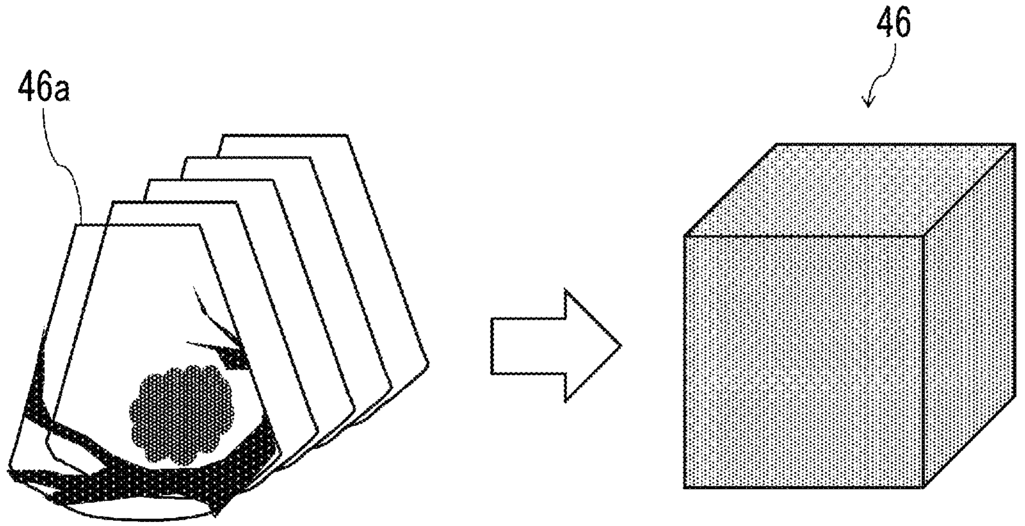
FIG. 10 is a conceptual diagram showing a concept of a process of forming volume data.

FIG. 10 is a conceptual diagram showing the concept of a process of forming the volume data 46. First, the model forming unit 54 forms the volume data 46 including the target tissue based on the received signal obtained by the transmission and reception of the ultrasound waves to and from the target tissue by the ultrasound probe 14. In the present embodiment, as shown in FIG. 10, the model forming unit 54 forms the volume data 46 based on a plurality of ultrasound tomographic images 46*a*. Since a known method can be used as a method of forming the volume data 46 from the plurality of ultrasound tomographic images 46*a*, a detailed description thereof will be omitted here.

The probe detection unit 50 detects the position and posture of the ultrasound probe 14 in a case where the ultrasound tomographic image 46*a* has been formed, and probe position and posture information indicating the position and posture of the ultrasound probe 14 detected by the probe detection unit 50 is associated with each ultrasound tomographic image 46*a*. The probe detection unit 50 performs the calibration in a state in which the ultrasound probe 14 is brought into contact with a prescribed position of the subject E in a prescribed posture. Therefore, the probe position and posture information indicates the position and posture relative to the prescribed position and the prescribed posture of the subject E. Each position (coordinates) on the ultrasound tomographic image 46*a* can be specified based on the position and posture of the ultrasound probe 14 in a case where the ultrasound tomographic image 46*a* has been formed. That is, it can be said that coordinate information indicating each position of the ultrasound tomographic image 46*a* is attached to each ultrasound tomographic image 46*a*. Therefore, the volume data 46 composed of the plurality of ultrasound tomographic images 46*a* also has coordinate information indicating each position of the volume data 46.

Figure 11:
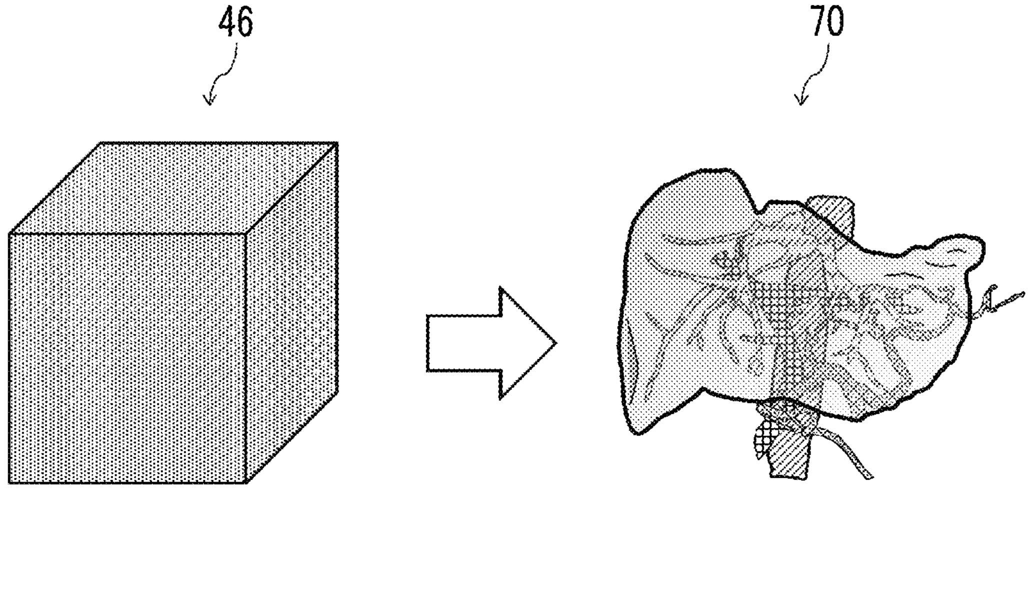
FIG. 11 is a conceptual diagram showing a concept of a process of forming a target tissue model.

FIG. 11 is a conceptual diagram showing the concept of a process of forming a target tissue model 70. The probe detection unit 50 forms the target tissue model 70 based on the volume data 46. Since a known method can be used as a method of forming the target tissue model 70 based on the volume data 46, a detailed description thereof will be omitted here. However, the model forming unit 54 forms the target tissue model 70 using a technique such as volume rendering or surface rendering. In a case where the volume data 46 has the coordinate information indicating each position, the target tissue model 70 also has position information (coordinates) indicating each position since the target tissue model 70 is formed from the volume data 46.

In the present embodiment, the target tissue model 70 is a three-dimensional model in which the shape of the target tissue is represented in three dimensions. However, the model forming unit 54 may form the target tissue model 70 which is a two-dimensional model. For example, the model forming unit 54 may project the three-dimensional target tissue model 70 in the depth direction of the subject E to form the two-dimensional target tissue model 70.

Even for the same organ (for example, the liver), the shape (including the size) of the organ usually differs depending on the subject E. In the present embodiment, the model forming unit 54 forms the target tissue model 70 representing the shape of the target tissue of the subject E based on the received signal obtained by transmitting and receiving the ultrasound waves to and from the subject E. Therefore, the target tissue model 70 represents the shape of the target tissue of the subject E. In other words, even for the target tissue models 70 indicating the same organ, the target tissue models 70 having different shapes are formed for each subject E.

Figure 12:
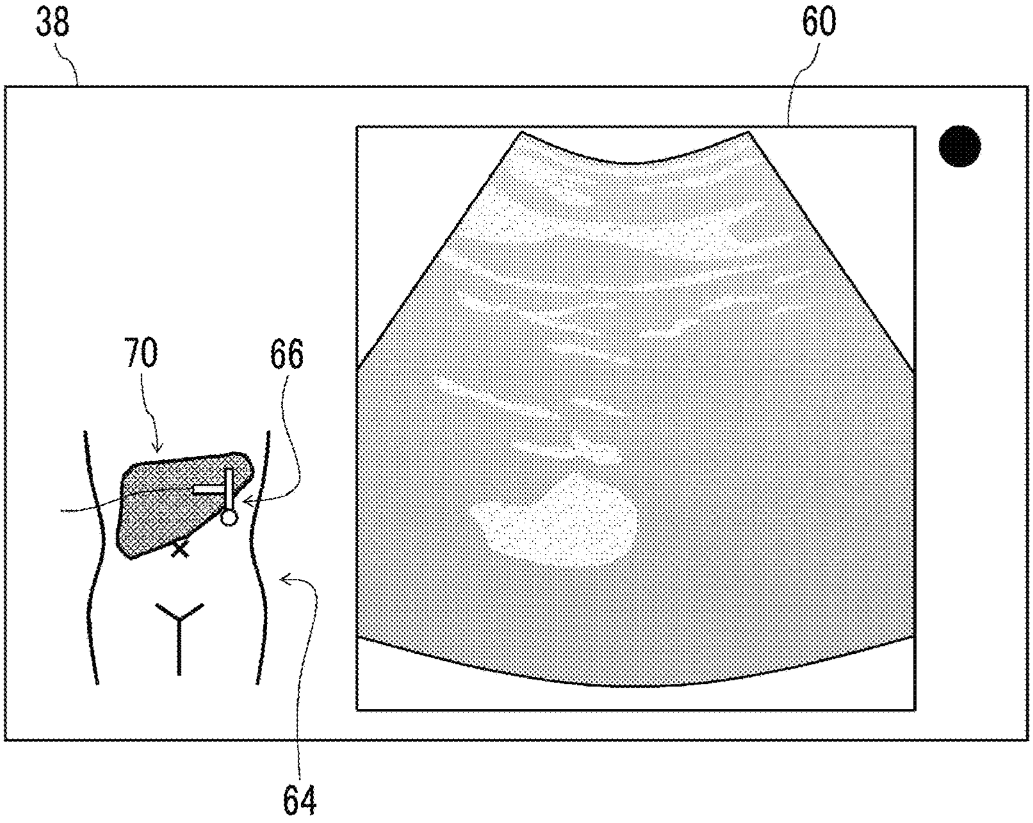
FIG. 12 is a diagram showing a display example of the ultrasound tomographic image and the target tissue model.

FIG. 12 is a diagram showing a display example of the ultrasound tomographic image 60 and the target tissue model 70. As shown in FIG. 5 or FIG. 7, the display controller 36 displays, on the display 38, the body mark 64 as the subject symbol schematically representing the outward shape of the subject E and the probe mark 66 as the probe symbol representing the position and posture of the ultrasound probe 14, together with the ultrasound tomographic image 60.

In the example shown in FIG. 12, the display controller 36 displays the target tissue model 70 formed by the model forming unit 54 to be superimposed on the body mark 64. As described above, since the target tissue model 70 also has the position information (coordinates) indicating each position, the display controller 36 can calculate the size and display position of the target tissue model 70 with respect to the body mark 64 based on the position information of the target tissue model 70 and the scale of the body mark 64.

Since the target tissue model 70 is displayed in addition to the body mark 64 and the probe mark 66, the operator can more suitably recognize which cross section of the subject E (particularly, the target tissue) the displayed ultrasound tomographic image 60 represents, based on the position of the probe mark 66 with respect to the target tissue model 70. In particular, as described above, since the target tissue model 70 represents the shape of the target tissue of the subject E, the target tissue model 70 more accurately represents the shape of the target tissue of the subject E, for example, as compared to a case where a model of a certain organ is prepared in advance and displayed. This enables the operator to more suitably recognize which cross section of the target tissue the ultrasound tomographic image 60 represents.

The lesion position detection unit 56 detects the position of a lesion part in the subject E. In particular, in the present embodiment, the lesion position detection unit 56 detects, as a lesion position, the position of the ultrasound probe 14 in a case where a lesion part is found in the ultrasound tomographic image 60 formed by transmitting and receiving the ultrasound waves to and from the subject.

First, the operator brings the ultrasound probe 14 into contact with the subject E, and the ultrasound waves are transmitted to and received from the subject E to acquire a received signal. The image forming unit 34 forms the ultrasound tomographic image 60 based on the received signal, and the display controller 36 displays a lesion specification screen including the ultrasound tomographic image 60 on the display 38.

Figure 13:
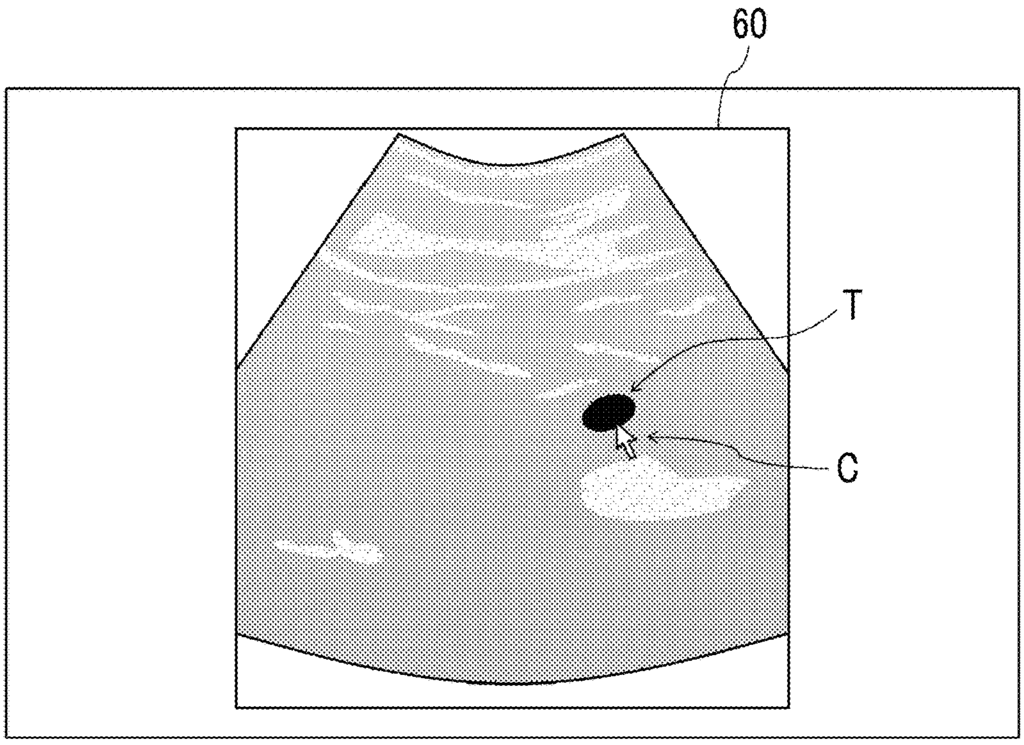
FIG. 13 is a diagram showing an example of a lesion specification screen.

FIG. 13 is a diagram showing a display example of the lesion specification screen. The operator checks the ultrasound tomographic image 60 displayed on the lesion specification screen and checks whether or not a lesion part T is included in the ultrasound tomographic image 60. In a case where the operator finds the lesion part T in the ultrasound tomographic image 60, the operator inputs a probe position specification instruction to the ultrasound diagnostic device 16 through the input interface 42. The lesion position detection unit 56 detects, as the lesion position, the position of the ultrasound probe 14 detected by the probe detection unit 50 in a case where the probe position specification instruction is input.

In addition, the operator may specify the position of the lesion part T in the ultrasound tomographic image 60, for example, using a cursor C such that the lesion position detection unit 56 further detects the depth at which the lesion part T is present.

Figure 14:
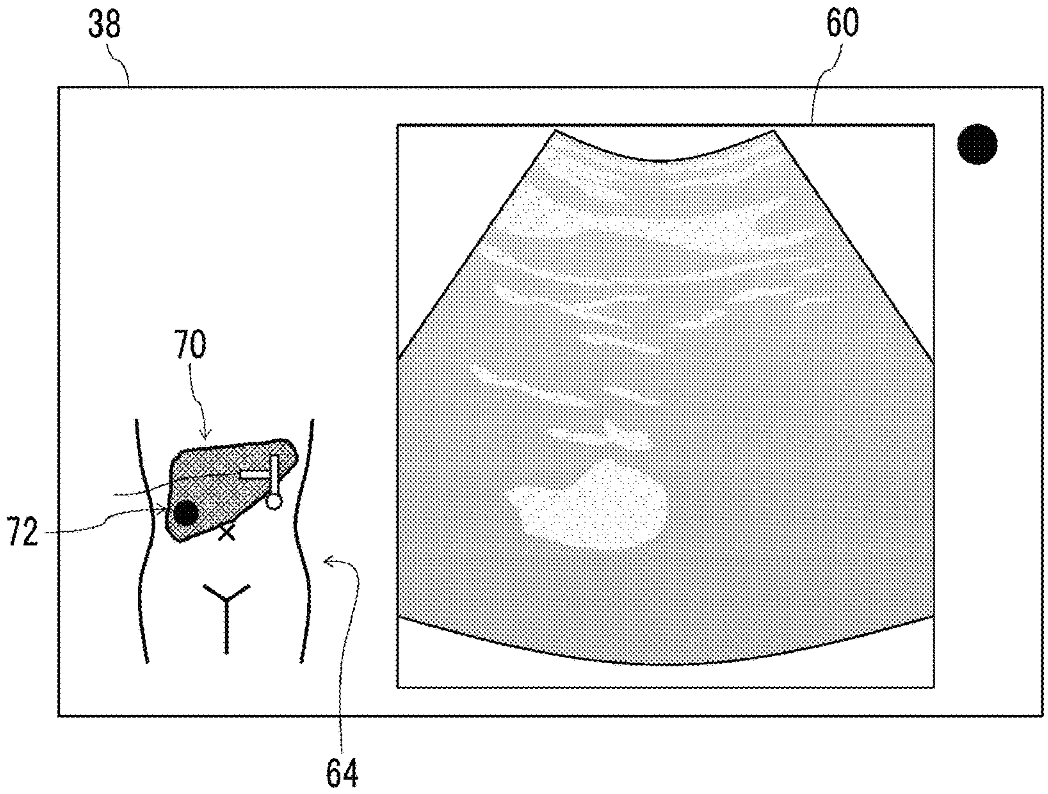
FIG. 14 is a diagram showing a first display example of the ultrasound tomographic image and a lesion position indicator.
Figure 15:
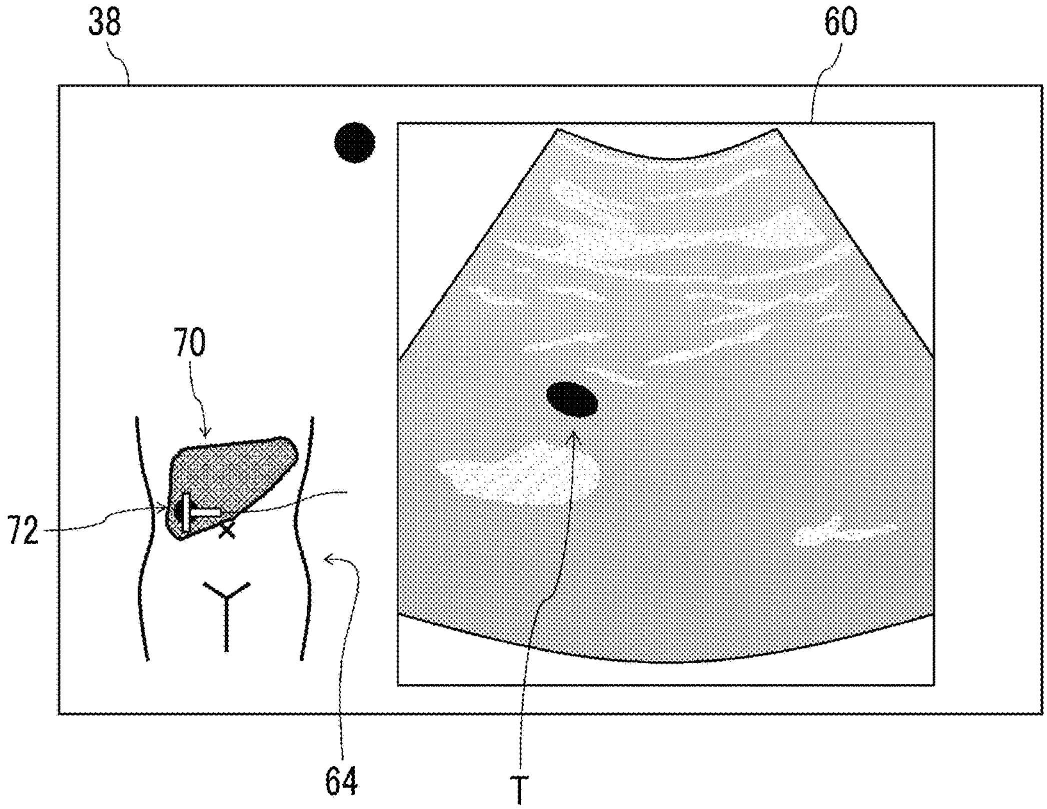
FIG. 15 is a diagram showing a second display example of the ultrasound tomographic image and the lesion position indicator.

FIG. 14 is a diagram showing a display example of the ultrasound tomographic image 60 and a lesion position indicator 72. The display controller 36 displays the lesion position indicator 72 indicating the lesion position detected by the lesion position detection unit 56 to be superimposed on the body mark 64. This enables the operator to easily identify the position of the lesion part T of the subject E. For example, as shown in FIG. 15, the operator can easily bring the ultrasound probe 14 onto the lesion position based on the lesion position indicator 72, that is, the operator can easily depict the lesion part T in the ultrasound tomographic image 60.

In particular, in a case where the lesion part T is detected in the target tissue of the subject E, the display controller 36 may display the lesion position indicator 72 to be further superimposed on the target tissue model 70 displayed to be superimposed on the body mark 64. In addition, in a case where the lesion position detection unit 56 detects the depth at which the lesion part T is present, the display controller 36 may also display information indicating the depth (for example, characters "depth of ○○ m") together.

Figure 16:
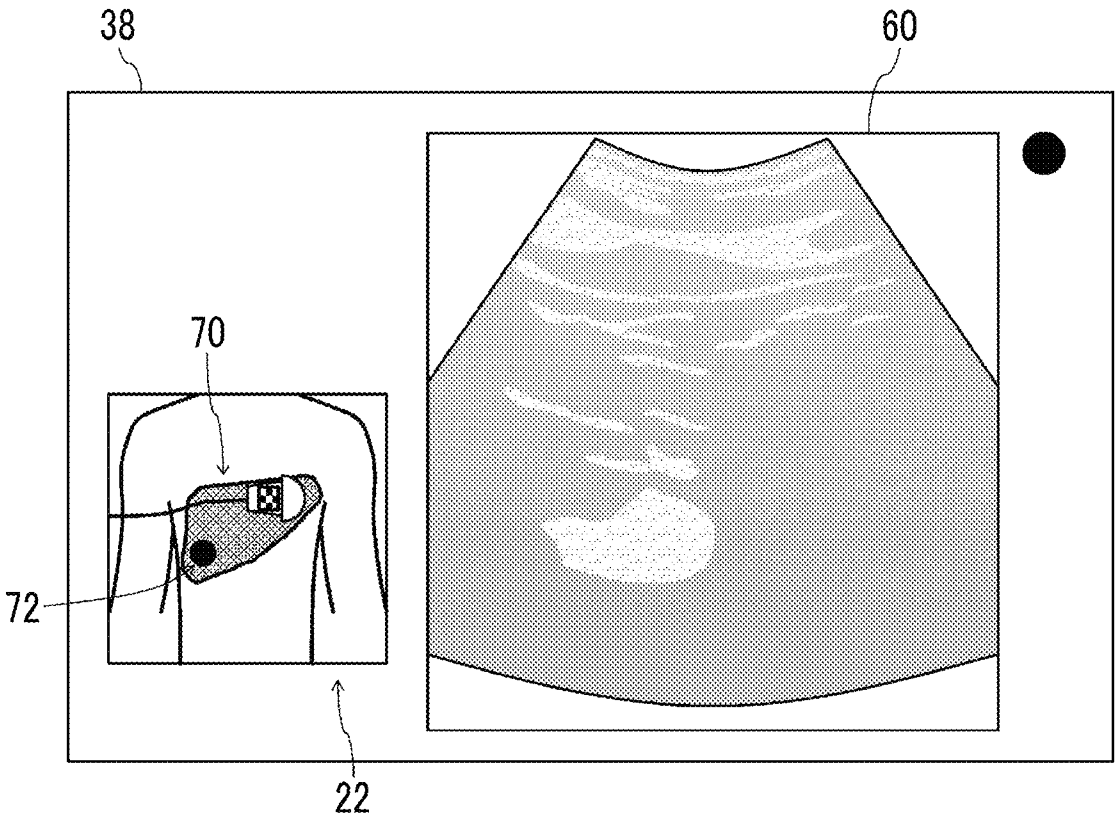
FIG. 16 is a diagram showing a display example of the ultrasound tomographic image, the captured image, the target tissue model, and the lesion position indicator.
Figure 17A:
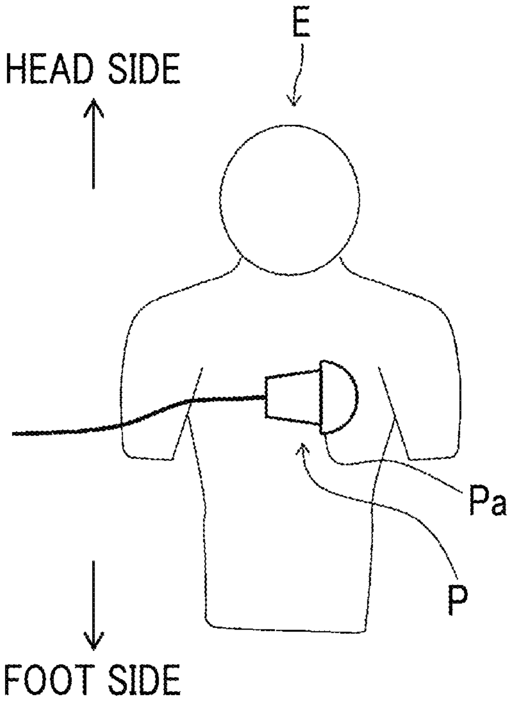
FIG. 17A is a diagram showing a first state in which an ultrasound probe is brought into contact with a subject in the related art.
Figure 17B:
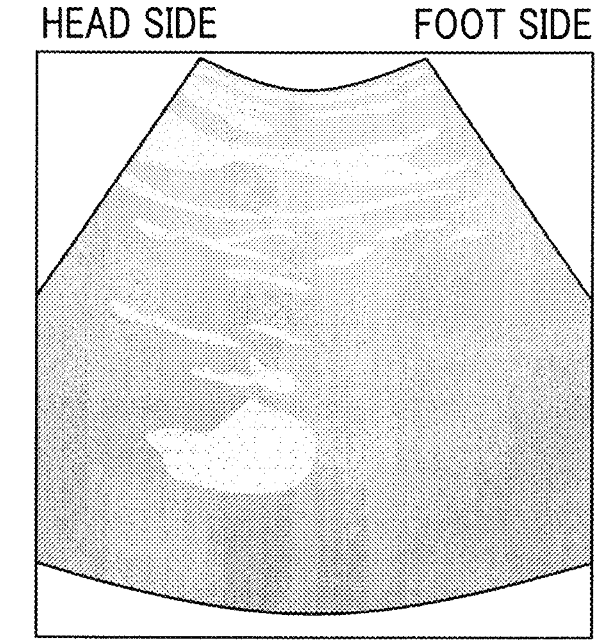
FIG. 17B is a diagram showing a display example of an ultrasound tomographic image that conforms to a display rule.
Figure 18A:
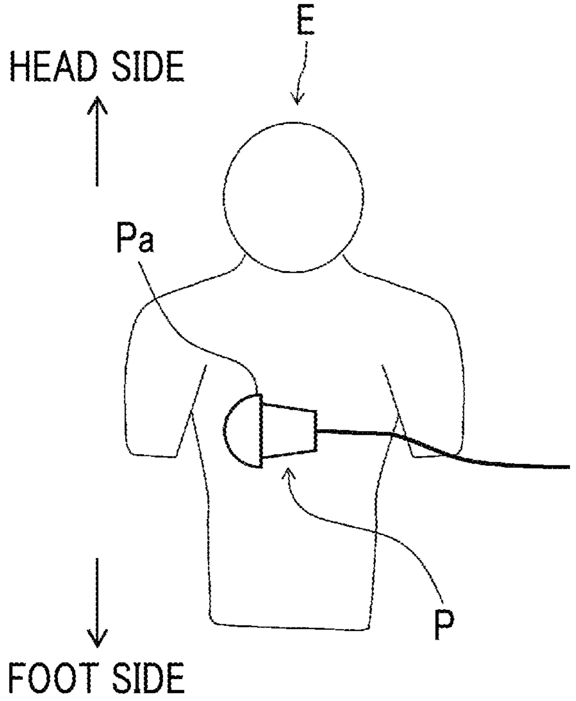
FIG. 18A is a diagram showing a second state in which the ultrasound probe is brought into contact with the subject in the related art.
Figure 18B:
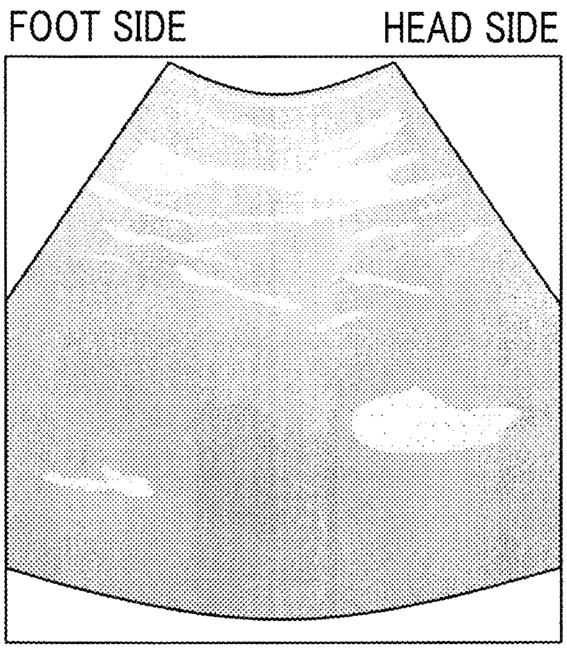
FIG. 18B is a diagram showing a display example of the ultrasound tomographic image that does not conform to the display rule.

FIG. 16 is a diagram showing a display example of the ultrasound tomographic image 60, the captured image 22, the target tissue model 70, and the lesion position indicator 72. As also shown in FIG. 8, the display controller 36 may display the captured image 22 formed by imaging the subject E and the ultrasound probe 14 using the camera 12 as the subject symbol and the probe symbol on the display 38, instead of the body mark 64 and the probe mark 66.

As shown in FIG. 16, the display controller 36 may display the target tissue model 70 to be superimposed on the captured image 22. In this case, since the target tissue model 70 representing the shape of the target tissue of the subject E is displayed on the captured image 22 on which the subject E and the ultrasound probe 14 are shown, the operator can quite accurately recognize which part of the subject E the displayed ultrasound tomographic image 60 represents in cross section.

Further, the display controller 36 may display the lesion position indicator 72 to be superimposed on the captured image 22. In this case, since the lesion position indicator 72 is displayed on the captured image 22 on which the subject E and the ultrasound probe 14 are shown, the operator can accurately identify the lesion position.

The ultrasound tomographic image display control device according to the embodiment of the present disclosure has been described above. However, the ultrasound tomographic image display control device according to the embodiment of the present disclosure is not limited to the above-described embodiment, and various modifications can be made without departing from the gist of the present disclosure.

For example, in each of the above-described embodiments, the ultrasound tomographic image display control device is the ultrasound diagnostic device 16, and the ultrasound diagnostic device 16 has each of the functions of the image forming unit 34, the display controller 36, the probe detection unit 50, the notification processing unit 52, the model forming unit 54, and the lesion position detection unit 56. However, the ultrasound diagnostic device 16 may not necessarily have each of these functions. For example, a server computer or the like that is connected to the ultrasound diagnostic device 16 such that the server computer or the like can communicate therewith may have these functions. In addition, one device may not have all of the above-described functions, but each of the above-described functions may be implemented by cooperation of a plurality of devices.

What is claimed is:

1. An ultrasound tomographic image display control device comprising:

a probe detection unit that detects a posture of an ultrasound probe which performs scanning with an ultrasound beam to transmit and receive an ultrasound wave to and from a target tissue of a subject; and a display controller that displays, on a display unit, an ultrasound tomographic image formed based on a received signal based on a reflected wave from the target tissue, wherein the display controller is configured to flip the ultrasound tomographic image horizontally and display the ultrasound tomographic image in a case where the posture of the ultrasound probe is a reversed posture in which one end side of a scanning direction of the ultrasound beam faces a direction opposite to a prescribed direction predetermined for the target tissue, and in a case where the ultrasound tomographic image is not in conformity with a display rule that defines a correspondence between a display direction of the target tissue and a direction in real space.

2. The ultrasound tomographic image display control device according to claim 1, wherein the display controller displays, on the display unit, an image orientation indicator indicating one end side of the ultrasound tomographic image in the scanning direction.

3. The ultrasound tomographic image display control device according to claim 1, wherein the display controller displays the ultrasound tomographic image on the display unit, without flipping the ultrasound tomographic image horizontally, even in a case where the ultrasound probe is in the reversed posture while the ultrasound probe is transmitting and receiving the ultrasound wave to and from the target tissue, and after the transmission and reception of the ultrasound wave to and from the target tissue are ended, the display controller flips the ultrasound tomographic image, which has been formed based on the received signal acquired while the ultrasound probe is in the reversed posture, horizontally and displays the ultrasound tomographic image on the display unit.

4. The ultrasound tomographic image display control device according to claim 1, wherein the probe detection unit further detects a position of the ultrasound probe, and the display controller displays a subject symbol that schematically represents an outward shape of the subject on the display unit, together with the ultrasound tomographic image, and further displays a probe symbol that represents the position and posture of the ultrasound probe to be superimposed on the subject symbol, based on the position and posture of the ultrasound probe detected by the probe detection unit.

5. The ultrasound tomographic image display control device according to claim 4, further comprising:

a camera that images the subject and the ultrasound probe, wherein the display controller displays an image captured by the camera as the subject symbol and the probe symbol on the display unit.

6. The ultrasound tomographic image display control device according to claim 1, further comprising:

a notification processing unit that, in a case where the probe detection unit is not capable of detecting a position or the posture of the ultrasound probe, notifies a user that the position or posture of the ultrasound probe is not capable of being detected.

7. A non-transitory computer-readable storage medium storing an ultrasound tomographic image display control program causing a computer to function as:

a probe detection unit that detects a posture of an ultrasound probe which performs scanning with an ultrasound beam to transmit and receive an ultrasound wave to and from a target tissue of a subject; and a display controller that displays, on a display unit, an ultrasound tomographic image formed based on a received signal based on a reflected wave from the target tissue, wherein the display controller is configured to flip the ultrasound tomographic image horizontally and display the ultrasound tomographic image in a case where the posture of the ultrasound probe is a reversed posture in which one end side of a scanning direction of the ultrasound beam faces a direction opposite to a prescribed direction predetermined for the target tissue, and in a case where the ultrasound tomographic image is not in conformity with a display rule that defines a correspondence between a display direction of the target tissue and a direction in real space.

* * * * *